US00PP22368P2

(12) United States Plant Patent
Meinl

(10) Patent No.: US PP22,368 P2
(45) Date of Patent: Dec. 20, 2011

(54) ***HYDRANGEA* PLANT NAMED 'HORHEART'**

(50) Latin Name: *Hydrangea macrophylla*
Varietal Denomination: Horheart

(75) Inventor: Katrin Meinl, Dresden (DE)

(73) Assignee: Claus & Tosten Kühne GbR, Dresden (DE)

( * ) Notice: Subject to any disclaimer, the term of this patent is extended or adjusted under 35 U.S.C. 154(b) by 0 days.

(21) Appl. No.: 12/798,735

(22) Filed: Apr. 10, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Hydrangea* plant named 'Horheart', characterized by its upright and mounded plant habit; strong and healthy root system; strong stems; and large mophead-type inflorescences with dark pink-colored flowers with white-colored margins.

2 Drawing Sheets

Botanical designation: *Hydrangea macrophylla.*
Cultivar denomination: 'HORHEART'.

BACKGROUND OF THE INVENTION

The present invention relates to a new and distinct cultivar of *Hydrangea* plant, botanically known as *Hydrangea macrophylla* and hereinafter referred to by the name 'Horheart'.

The new *Hydrangea* plant is a product of a planned breeding program conducted by the Inventor in Dresden, Germany. The objective of the breeding program was to develop new container-type *Hydrangea* plants with attractive leaf, stem and flower coloration.

The new *Hydrangea* plant originated from a cross-pollination in August, 2002 of *Hydrangea macrophylla* 'Moritzburg', not patented, as the female, or seed parent and a proprietary selection of *Hydrangea macrophylla* identified as code number 68-9717, not patented, as the male, or pollen, parent. The new *Hydrangea* plant was discovered and selected by the Inventor during the summer of 2004 as a flowering plant within the progeny of the stated cross-pollination in a controlled environment in Dresden, Germany.

Asexual reproduction of the new cultivar by softwood cuttings in Dresden, Germany since June, 2005 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Horheart'. These characteristics in combination distinguish 'Horheart' as a new and distinct cultivar of *Hydrangea* plant:

1. Upright and mounded plant habit.
2. Strong and healthy root system.

3. Strong stems.
4. Large mophead-type inflorescences with dark pink-colored flowers with white-colored margins.

Plants of the new *Hydrangea* differ primarily from plants of the female parent, 'Moritzburg', in flower color as plants of 'Moritzburg' have solid pink-colored flowers.

Plants of the new *Hydrangea* differ primarily from plants of the male parent selection in growth habit as plants of the new *Hydrangea* are more compact than and not as vigorous as plants of the male parent selection. In addition, plants of the new *Hydrangea* have stronger root systems and stems than plants of the male parent selection.

Plants of the new *Hydrangea* can be compared to plants of *Hydrangea* 'Harlequin', not patented. Plants of the new *Hydrangea* differ primarily from plants of 'Harlequin' in the following characteristics:

1. Plants of the new *Hydrangea* have stronger root systems than plants of 'Harlequin'.
2. Plants of the new *Hydrangea* are more vigorous than plants of 'Harlequin'.
3. Plants of the new *Hydrangea* have stronger stems than plants of 'Harlequin'.
4. Flowers of plants of the new *Hydrangea* have larger sepals than flowers of plants of 'Harlequin'.
5. Sepal margins of plants of the new *Hydrangea* are entire whereas sepal margins of plants of 'Harlequin' are serrate.

BRIEF DESCRIPTION OF THE PHOTOGRAPHS

The accompanying colored photographs illustrate the unique appearance of the new *Hydrangea* plant, showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Horheart' grown in a container.

The photograph on the second sheet is a close-up view of a typical inflorescence of 'Horheart'.

DETAILED BOTANICAL DESCRIPTION

Plants used in the aforementioned photographs and in the following description were grown during the summer and autumn in Grand Haven, Mich. in an outdoor nursery and under conditions which closely approximate commercial production conditions. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea macrophylla* 'Horheart'.

Parentage:

*Female, or seed, parent.*—*Hydrangea macrophylla* 'Moritzburg', not patented.

*Male, or pollen, parent.*—Proprietary selection of *Hydrangea macrophylla* identified as code number 68-9717, not patented.

Propagation:

*Type cutting.*—By softwood cuttings.

*Time to initiate roots.*—About 18 days at temperatures about 24° C.

*Time to produce a rooted young plant.*—About 60 days at temperatures about 24° C.

*Root description.*—Strong and healthy root system; roots fine to thick; creamy white in color.

*Rooting habit.*—Freely branching; dense.

Plant description:

*Form/growth habit.*—Perennial shrub; upright and mounded plant habit; broadly inverted triangle; freely branching habit, about 35 lateral branches develop per plant; strong lateral branches; vigorous growth habit.

*Plant height.*—About 60 cm.

*Plant diameter or area of spread.*—About 50 cm.

*Lateral branches.*—Length: About 38 cm. Diameter: About 4 mm. Internode length: About 8 cm. Texture: Smooth, glabrous. Strength: Very strong. Aspect: Erect to about 30° from vertical. Color, young: Close to 143B. Color, developed: Close to 166C to 166D.

Foliage description:

*Arrangement.*—Opposite, simple.

*Length.*—About 12.5 cm.

*Width.*—About 7 cm.

*Shape.*—Broadly ovate.

*Apex.*—Acute.

*Base.*—Cuneate to obtuse.

*Margin.*—Serrate.

*Texture, upper and lower surfaces.*—Smooth, glabrous; rugose.

*Venation pattern.*—Pinnate.

*Color.*—Developing leaves, upper surface: Close to 139A. Developing leaves, lower surface: Close to 146B. Fully expanded leaves, upper surface: Close to 139A; venation, close to 146C. Fully expanded leaves, lower surface: Close to 146A; venation, close to 146C.

*Petiole.*—Length: About 2 cm. Diameter: About 4 mm. Texture, upper and lower surfaces: Smooth, glabrous. Color, upper and lower surfaces: Close to 146C.

Flower description:

*Flower type and habit.*—Single sterile and inconspicuous fertile flowers arranged on terminal mophead-type panicles; fertile flowers face mostly upright and sterile flowers face mostly upright to outwardly.

*Fragrance.*—None detected.

*Natural flowering season.*—Continuous flowering from June to September in Grand Haven, Mich.

*Flower longevity, fertile flowers.*—Flowers last about two weeks on the plant; flowers not persistent.

*Flower longevity, sterile flowers.*—Flowers last about three months on the plant; flowers persistent.

*Quantity of flowers.*—Freely flowering; about nine fertile flowers and about 69 sterile flowers per panicle.

*Panicle height.*—About 10 cm.

*Panicle diameter.*—About 16 cm.

*Flower diameter, fertile flowers.*—About 4 mm.

*Flower depth (height), fertile flowers.*—About 5 mm.

*Flower diameter, sterile flowers.*—About 5 cm.

*Flower depth (height), sterile flowers.*—About 3 cm.

*Flower buds, fertile and sterile flowers.*—Length: About 2 mm. Diameter: About 1 mm. Shape: Ovate. Color: Close to 66D.

*Petals, fertile flowers only.*—Quantity/arrangement: Five in a single whorl. Length: About 2 mm. Width: About 1 mm. Shape: Elliptic. Apex: Acute. Base: Attenuate. Margin: Entire. Texture, upper and lower surfaces: Smooth, glabrous. Color: When opening, upper and lower surfaces: Close to 66B. Fully opened, upper and lower surfaces: Close to 66B.

*Sepals, fertile flowers.*—Quantity/arrangement: Five in a single whorl. Length: About 1 mm. Width: About 0.5 mm to 1 mm. Shape: Lanceolate. Apex: Acute. Base: Fused. Margin: Entire. Texture, upper and lower surfaces: Smooth, glabrous. Color, upper and lower surfaces: Close to 66B.

*Sepals, sterile flowers.*—Quantity/arrangement: Four in a single whorl. Length: About 2.2 cm. Width: About 2.5 cm. Shape: Broadly ovate. Apex: Acute to obtuse. Base: Broadly cuneate. Margin: Entire. Texture, upper and lower surfaces: Smooth, glabrous. Color: When opening and fully opened, upper surface: Color can range from between 67A and 53B; margins, close to 155D; margins about 3 mm in width. When opening and fully opened, lower surface: Color can range from between 73B and 67A; margins, close to 155D.

*Peduncles, fertile and sterile flowers.*—Angle: Erect to about 45° from vertical. Strength: Strong. Length: About 3.5 cm. Diameter: About 3 mm. Texture: Smooth, glabrous. Color: Close to 141C.

*Pedicels, fertile flowers.*—Angle: Erect to about 10° from vertical. Strength: Moderately strong. Length: About 3 mm. Diameter: About 1 mm. Texture: Smooth, glabrous. Color: Close to 58C.

*Pedicels, sterile flowers.*—Angle: Erect to about 40° from vertical. Strength: Strong. Length: About 2.4 cm. Diameter: About 2 mm Texture: Smooth, glabrous. Color: Close to 58B.

*Reproductive organs, fertile flowers only.*—Stamens: Quantity per flower: About five. Anther length: About 0.5 mm. Anther shape: Oblong. Anther color: Close to 188C. Pollen amount: Moderate. Pollen color: Close to 188C. Pistils: Pistil quantity per flower: About three. Pistil length: About 3 mm. Stigma shape:

Oblong. Stigma color: Close to 58D. Style length: About 1 mm. Style color: Close to 158D. Ovary color: Close to 149D.

*Seeds.*—Length: Less than 0.5 mm. Diameter: Less than 0.5 mm. Color: Brownish, close to 200A in color.

Disease/pest resistance: Plants of the new *Hydrangea* have not been observed to be resistant to pathogens and pests common to *Hydrangea*.

Temperature tolerance: Plants of the new *Hydrangea* have been shown to be tolerant to temperatures ranging from about −25° C. to about 38° C.

It is claimed:

1. A new and distinct *Hydrangea* plant named 'Horheart' as illustrated and described.

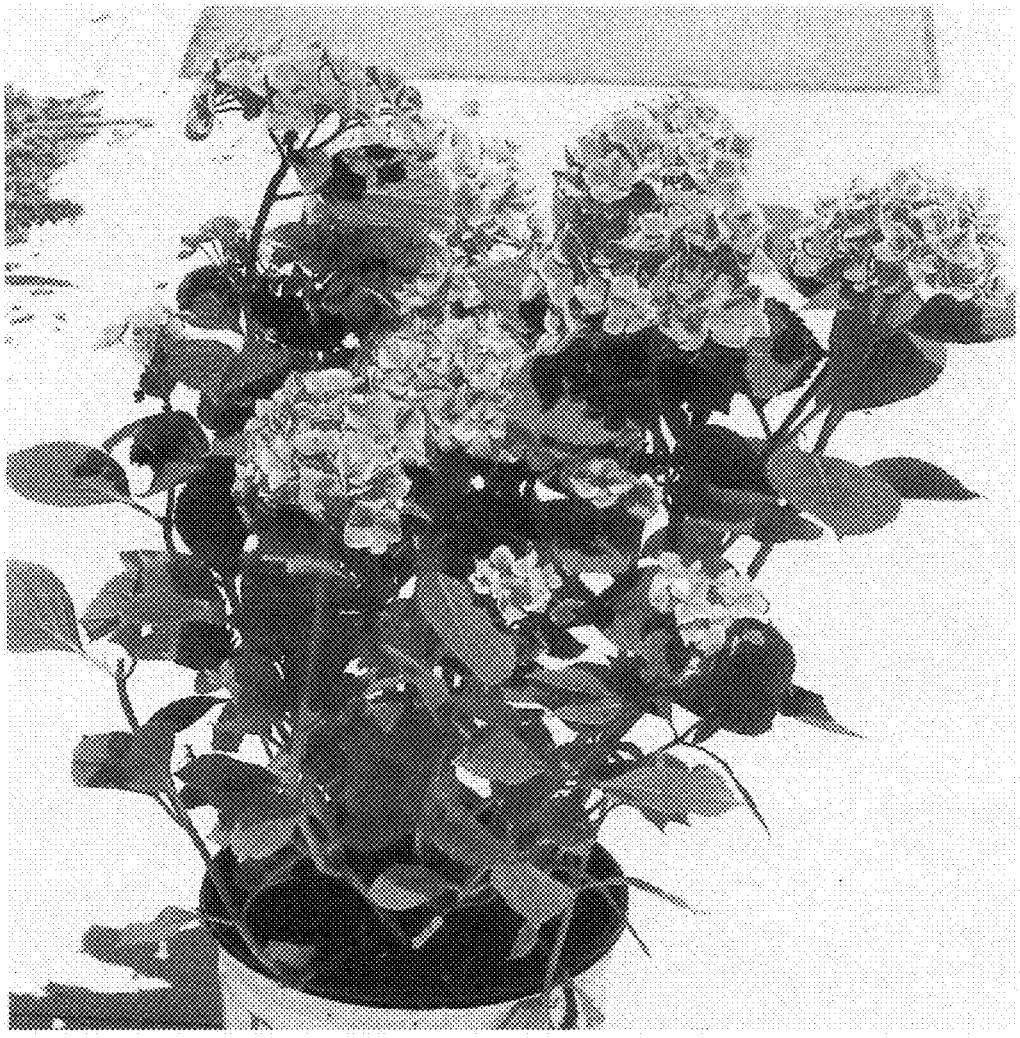

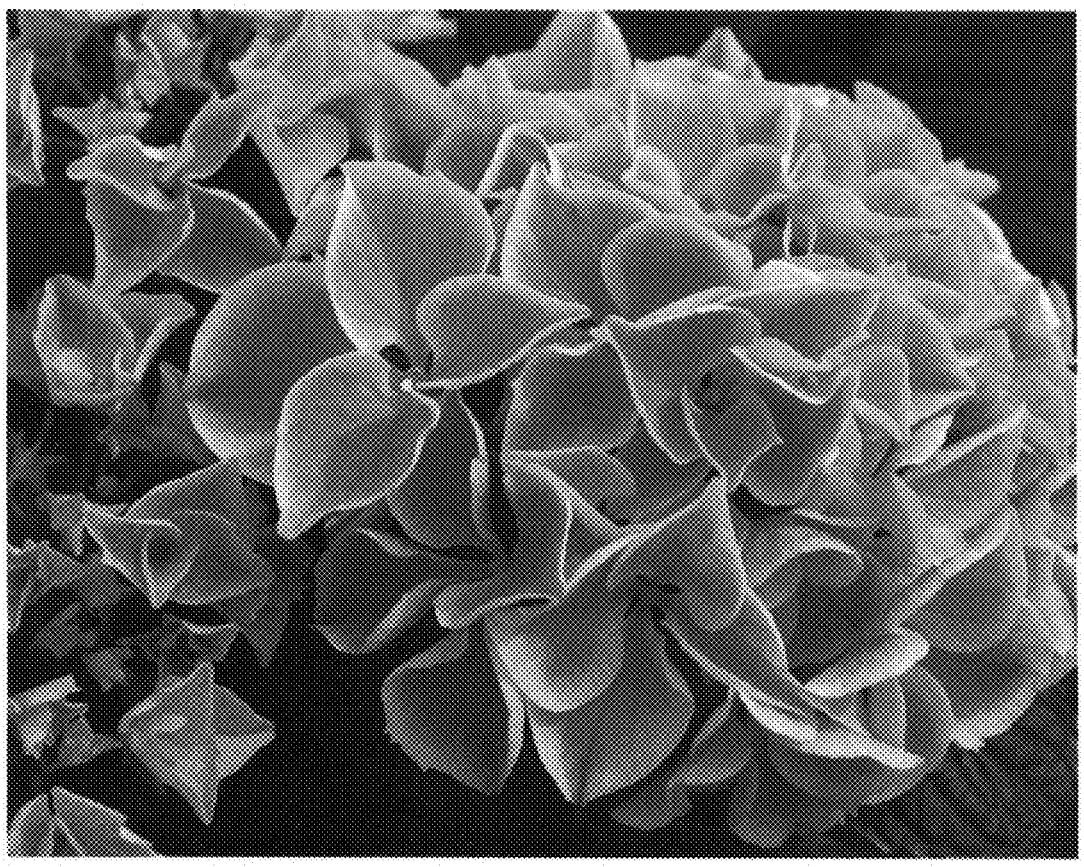

* * * * *